United States Patent

Korwin et al.

Patent Number: 4,470,505
Date of Patent: Sep. 11, 1984

[54] METHOD AND APPARATUS FOR STORING, MIXING AND DELIVERING DENTAL AMALGAM

[76] Inventors: Paul Korwin, 150-09 77th Ave., Flushing, N.Y. 11367; Robert Korwin, 56 Kingsley Way, Freehold, N.J. 07728

[21] Appl. No.: 461,262

[22] Filed: Jan. 26, 1983

[51] Int. Cl.³ ............................................. B65D 25/08
[52] U.S. Cl. .................................. 206/219; 206/63.5; 206/221; 222/136; 222/386; 604/87
[58] Field of Search .................. 206/63.5, 219, 220, 206/221, 222; 215/6, 32, 33, 247; 222/61, 136, 386; 604/87, 89, 416; 141/329, 330

[56] References Cited

U.S. PATENT DOCUMENTS

| | | | |
|---|---|---|---|
| 3,439,823 | 4/1969 | Morane | 206/221 |
| 3,467,097 | 9/1969 | Ogle | 206/221 |
| 3,477,431 | 11/1969 | Walecka | 604/89 |
| 3,595,439 | 7/1971 | Newby | 222/136 |
| 3,860,114 | 1/1975 | Merckardt | 206/219 |
| 4,193,698 | 3/1980 | Gartner | 206/219 |

Primary Examiner—Joseph Man-Fu Moy
Assistant Examiner—David Fidei
Attorney, Agent, or Firm—Alexis Barron; Richard D. Weber

[57] ABSTRACT

An amalgam capsule includes two chambers separated by a piston detachably formed as a part of the capsule end cover. One compartment is formed in part by a resilient flange portion of the capsule which is deformable to provide communication of the chambers and to permit a mixing of the contents of the chambers in the larger of the chambers. Delivery of the mixed amalgam is accomplished by removing a cap from one end of the capsule to expose an aperture therein, and connecting the opposite cover end of the capsule to a syringe, the plunger of which detaches the piston from the capsule cover and drives the piston through the mixing chamber to eject the amalgam therefrom.

9 Claims, 4 Drawing Figures

U.S. Patent
Sep. 11, 1984
4,470,505
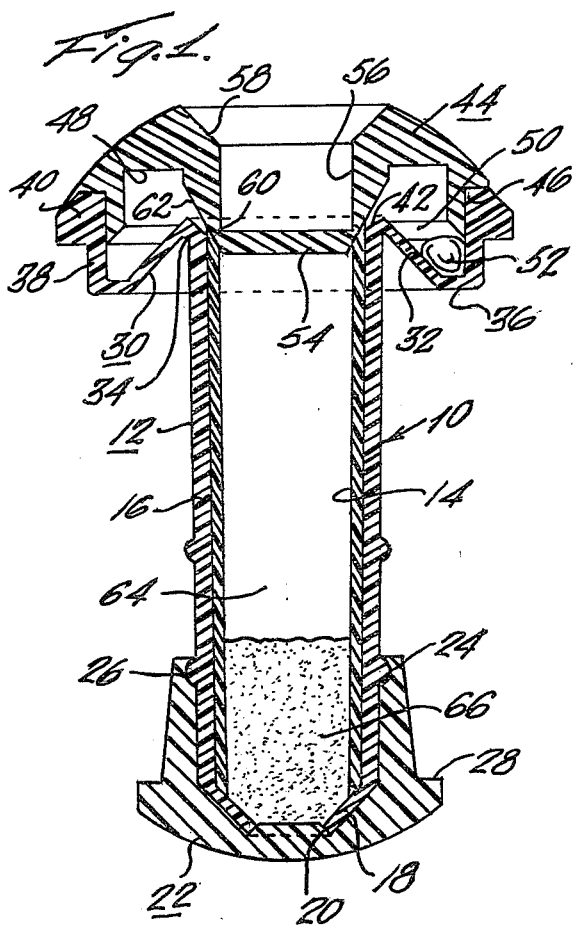
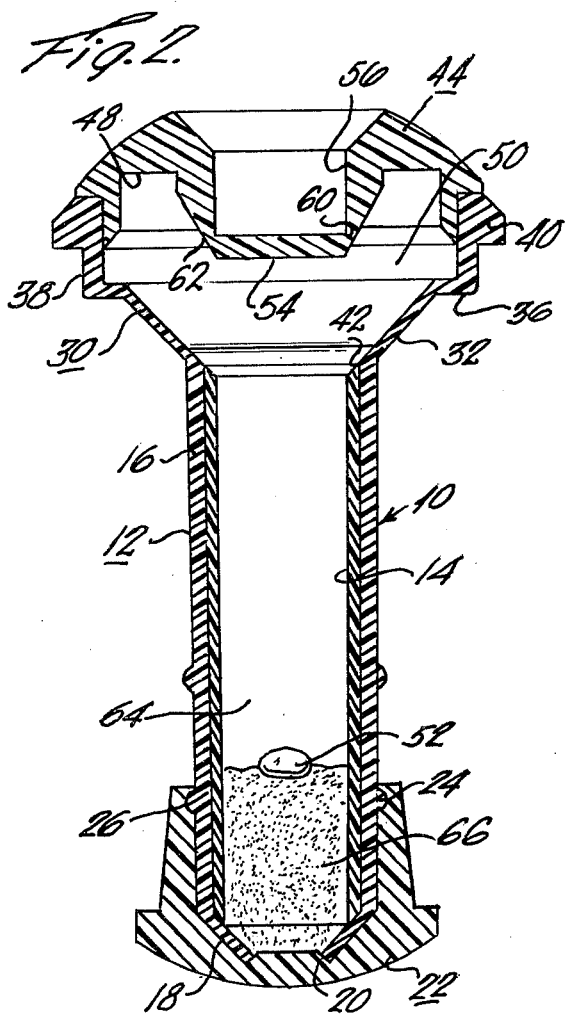
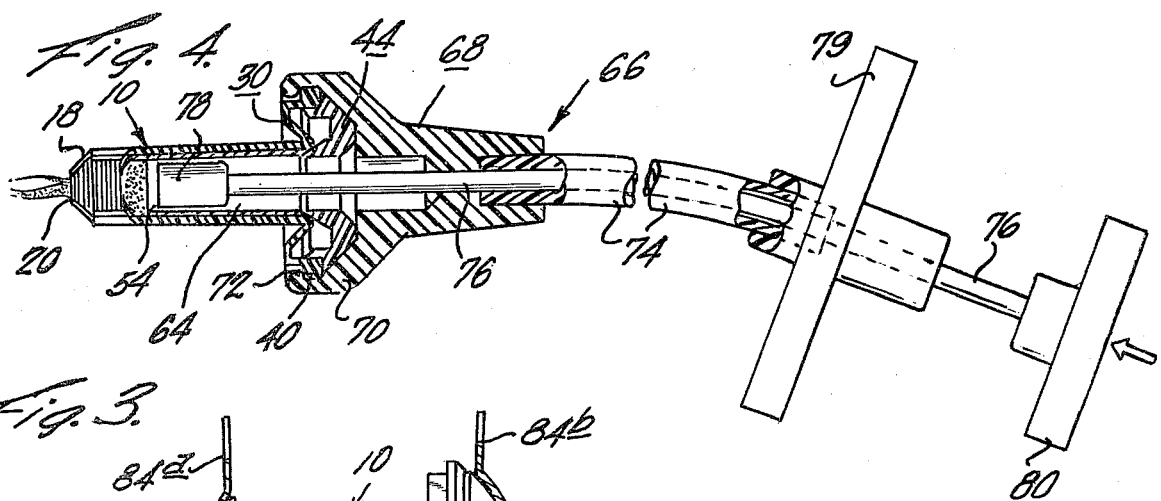
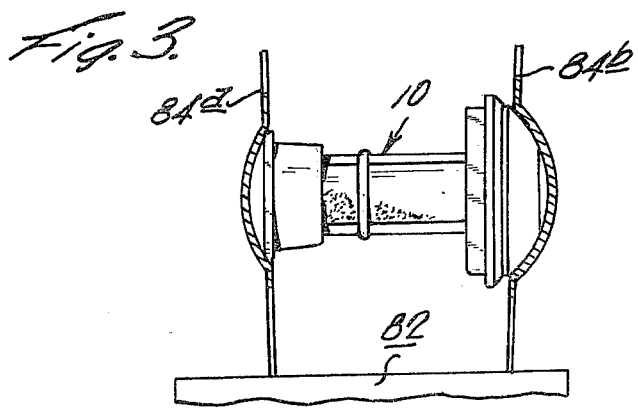

METHOD AND APPARATUS FOR STORING, MIXING AND DELIVERING DENTAL AMALGAM

BACKGROUND OF THE INVENTION

The present invention relates generally to the preparation and delivery of dental amalgam and relates more particularly to a method and apparatus wherein the amalgam constituents are stored and mixed in, and delivered from, a sealed capsule.

Dental amalgams conventionally include an alloy of various metals in powdered form which is mixed with mercury just prior to application to a prepared dental cavity. In early dentistry, the amalgam ingredients were mixed in an open vessel and the proportions were gauged by the viscosity of the mixture. As dental techniques improved, it was recognized that more careful attention to the proportions of the ingredients was desirable and systems were devised whereby the amalgam ingredients were prepackaged in capsules in the correct proportions. Transfer from prepackaged capsules to the mouth still involved the use of open vessels with the opportunity of contamination of the amalgam by foreign matter and bacteria, and contamination of the environment by spillage and vaporization of mercury.

The belated recognition of the toxic nature of mercury vapors and the dangers inherent in any procedure which permit the exposure of the mercury or the amalgam to the atmosphere has resulted in the proposal of a number of systems for storing, mixing and dispensing the amalgam to minimize such exposure.

In U.S. Pat. No. 1,774,258, for example, a capsule is provided having separate compartments within which the amalgam ingredients may be separately stored. When the amalgam is needed, the membrane separating the compartments is broken and the mixing of the ingredients is accomplished by placing the capsule in a mixing machine. For delivery to a patient, however, the amalgam must be placed in an open container for pickup by an amalgam applicator and hence this particular approach eliminates only a part of the problem, namely the proportioning of the ingredients and the isolation thereof from the atmosphere during storage and mixing. Other forms of capsules for storing and mixing of dental materials are shown in U.S. Pat. Nos. 2,527,991 and 3,638,918.

Later developments recognized the desirability of dispensing the amalgam directly from the container in which it was mixed into the prepared dental cavity. Patents exemplifying such a system include U.S. Pat. Nos. 3,368,592, 3,521,356, 3,724,077 and 3,828,434. In none of these arrangements, however, does it appear that the amalgam constituents are packaged and stored in the container in which the mixing takes place.

More recent developments have attempted to combine the storage, mixing and delivery functions in the same container or capsule. For instance, in U.S. Pat. No. 3,760,503 the ingredients are brought together by the puncturing of the compartment holding one component by a spatula which is then rotated to mix the ingredients. When mixing is completed, the spatula is withdrawn and a plunger inserted to deliver the mixture from the opposite end of the container.

U.S. Pat. No. 4,084,320, discloses a structurally complex capsule having rotatable and removeable end members which are rotated to provide communication of the mercury with the powder materials, again rotated to provide a mixing of the materials, and then removed and replaced by special spout and plunger elements for delivery of the amalgam.

Although various types of capsule systems have been made commercially available, they have not, for various reasons, become popular, and dentists today are still to a large extent using techniques which involve the placement of the amalgam on an open surface for piecemeal transfer to the cavity in an amalgam carrier. Not only do such techniques permit the release of toxic mercury vapors, but they also permit contamination of the amalgam by exposure to contaminents on the surface, in the air, and especially in the amalgam carrier which is repeatedly exposed to the bacteria of different patients' mouths.

BRIEF DESCRIPTION OF THE INVENTION

The present invention provides an improved amalgam capsule and a method of storing, mixing and applying the amalgam by use of such a capsule which simplifies the procedures and structural components employed by the prior art. Specifically, the invention includes a capsule having two chambers which are separated by a piston detachably formed as a part of the capsule end cover. The compartment carrying the fluid ingredient such as mercury is formed in part by a flange portion of the capsule body which is deformable upon the application of an axial force to provide communication of the chambers and the flow of the mercury into the larger, central mixing chamber. Mixing is accomplished by placing the capsule in a conventional mixing machine.

Delivery of the amalgam mixture is effected by removing a cap from one end of the capsule to expose an aperture therein, and connecting the opposite end of the capsule to a syringe, the plunger of which detaches the piston from the capsule cover and drives the piston through the mixing chamber to eject the amalgam therefrom.

In the preferred embodiment, the flange portion of the capsule body forming a part of the fluid chamber is configured at an acute angle to the cylindrical chamber body wall, preferably about 45°, such that axial deformation of the capsule will cause the resilient flange to spring over center, thereby providing a positive and unmistakeable opening of the fluid chamber into the mixing chamber which assures that all of the mercury has an opportunity to pass into the mixing chamber. Upon release, the resilient flange returns the capsule to its storage condition, again sealing the chambers with all of the amalgam constituents in the mixing chamber.

With the present capsule, the amalgam is not exposed to the ambient air until the mixed amalgam is delivered from the capsule directly to the prepared cavity and accordingly there is no opportunity for mercury vapors to escape into the atmosphere or contaminents to reach the amalgam or its constituents prior to delivery to the patient's teeth.

It is accordingly a first object of the present invention to provide an improved amalgam capsule and method for storing, mixing and delivering a dental amalgam.

Another object of the invention is to provide a capsule and method as described which will substantially eliminate the contamination of the air by release of vapors and the contamination of the amalgam by the exposure to equipment and airborne contaminents.

An additional object of the invention is to provide a method and apparatus as described which prevents waste of the amalgam by eliminating spillage and by permitting delivery of all of the mixed amalgam to the prepared cavity.

Still another object of the invention is to provide a method and apparatus as described wherein the amalgam carrier system is disposable, thus eliminating the need for amalgam carriers and amalgam wells, preventing transfer of disease and providing a consistent viscosity of the amalgam.

A further object of the invention is to provide a method and apparatus as described wherein the communication of the capsule chambers is provided by an elastic deformation of a portion of the capsule and does not involve the puncturing, breaking or removal of internal capsule partitions.

Another object of the invention is to provide a method and apparatus as described wherein the deformation of the capsule to provide communication of the capsule chambers is effected by a simple application of an axial elongating force to the capsule body to produce a substantial and unmistakeable snap-action elongation of the capsule.

Still another object of the invention is to provide a method and apparatus as described wherein the condition of the capsule and its contents may be visually ascertained during any step of the method.

An additional object of the invention is to provide an amalgam capsule which can be used with conventional mixing devices.

Another object of the invention is to provide a method and apparatus as described which saves time, which can be economically put into practice and which greatly simplifies the preparation and application of dental amalgam.

Additional objects and advantages of the invention will be more readily apparent from the following detailed description of a preferred embodiment thereof.

BRIEF DESCRIPTION OF THE DRAWINGS

FIG. 1 is a longitudinal sectional view of a capsule for dental amalgam made in accordance with the present invention and showing the amalgam constituents in a stored condition;

FIG. 2 is a view similar to FIG. 1 showing the capsule just after the elongation thereof to provide communication of the capsule chambers and the introduction of the mercury to the powdered materials;

FIG. 3 is a view showing the capsule of FIGS. 1 and 2 in reduced scale positioned in an amalgamator for mixing of the amalgam; and FIG. 4 is a view showing the capsule of FIGS. 1 and 2 in reduced scale connected with a syringe and in the process of delivering the mixed amalgam.

DESCRIPTION OF THE PREFERRED EMBODIMENT

Referring to the drawings and particularly FIG. 1 thereof, the capsule 10 of the present invention comprises a capsule body 12 which is essentially of a hollow elongated cylindrical shape. In the preferred embodiment, the capsule body 12 includes an inner cylindrical sleeve 14 of a rigid material, an an outer body member 16 of a resilient, relatively flexible material.

The capsule body terminates at one end in a conical nozzle portion 18 formed only by the resilient body member 16 for a purpose explained below. A circular aperture 20 at the end of the nozzle portion 18 coaxial with the cylindrical body is closed during the storage and mixing uses of the capsule by a cap 22. The cap is preferably made of an elastic material which provides an airtight seal of the aperture 20 but which can be readily removed to permit delivery of the amalgam through the aperture following the mixing thereof. An annular bead 24 on the capsule body member 16 cooperates with an annular groove 26 of the cap to provide a resilient attachment of the cap which can be released by a sufficient axial withdrawing force applied to the cap. To facilitate the cap removal, an annular shoulder 28 is provided around the cap periphery.

At the end of the capsule body opposite the apertured end, the body includes an annular flange 30 extending from the outer body member 16. The flange 30 includes a thinwalled angled portion 32 extending from the end 34 of the cylindrical portion of the body, the angled portion 32 forming preferably about a 45° angle with respect to the cylindrical portion of the capsule body. The angled portion 32 thus forms an outwardly sloping frusto-conical surface in the normal storage position of the capsule. At the outer end of the angled portion 32, the flange continues in a short radial section 36 which in turn joins with an axial portion 38 terminating in a shoulder portion 40. The portions 36, 38 and 40 of the flange are of a thicker wall section than the angled portion 32 and are thus somewhat less flexible. The end of the sleeve 14 and the adjacent end of the cylindrical portion of the body member 16 are of a beveled configuration and thus provide a conical seating surface 42 having an angle of approximately 45° with respect to the axis of the capsule body portion.

The capsule also includes a cover 44 having an annular peripheral groove 46 permitting connection with the shoulder 40 of flange 30 in sealing relation by means of a suitable adhesive. The cover 44 includes an annular internal channel 48 which is disposed essentially opposite the angled portion 32 of the flange and forms in conjunction with the portions 32, 36 and 38 of the flange a chamber 50 adapted for the storage of fluid material such as a ball 52 of mercury as illustrated in FIG. 1. The chamber 50 is sealed from the space within the cylindrical portion of the capsule by means of a detachable piston 54 which is formed as an integral part of the cover. A cylindrical bore 56 in the cover extends to the outer surface of the piston, the bore 56 having an outwardly flaring portion 58 adjacent the outer end thereof. The piston 54 is joined to the main portion of the cover 44 by a narrow annular neck 60 which is defined on one side by the bore 56 and on the other side by a frusto-conical surface 62 having an included angle smaller than that of the conical surface 42. The cover 44 is dimensioned such that the surfaces 62 and 42 will engage in tight sealing contact to prevent communication between the chamber 50 and the interior of the cylindrical portion of the capsule.

The closures provided by the piston 54 and the cap 22 at the opposite ends of the capsule body 12 defines therewithin a sealed mixing chamber 64 within which a quantity of powdered amalgam ingredients 66 may be stored. The contents of the chamber 64 are securely sealed from the contents of chamber 50 by the piston 54 and the sealing engagement of the surfaces 42 and 62.

The capsule as illustrated in FIG. 1 with the mercury 52 sealed in chamber 50 and the powder material 66 sealed in chamber 64 is in the form in which the capsule is delivered to dentists from a dental supply house. The capsules may be stored indefinitely prior to use and present no danger of contamination of the atmosphere since there are no orifices or gaps such as screw threads through which the mercury vapors can pass. Similarly, the amalgam ingredients are protected from contamination from the atmosphere since each capsule is hermetically sealed. Additional protection may of course be provided by appropriate sealing of shipping and storage containers bearing a number of the capsules. With the preferred use of transparent materials for the capsule, the condition of the capsule contents may be examined during storage.

To prepare the amalgam, the capsule is resiliently deformed to permit communication between the chambers 50 and 64 and the passage of the mercury 52 into the chamber 64 for mixing with the powdered material 66. This is accomplished by simply grasping the cylindrical portion of the capsule body 12 in a vertical position in one hand and pulling axially upwardly on the outer portion of the flange 30 with the other hand to reverse the inclination of the frusto-conical surface formed by the angled flange portion 32 as shown in FIG. 2. The thin walled resilient nature of the portion 32 permits the elastic deformation shown and results in the separation of the surfaces 42 and 62, thereby providing a wide opening of the chamber 50. The reversal of the angled portion 32 of the flange as shown in FIG. 2 forms a funnel shaped surface serving to direct the entire contents of the chamber 50 downwardly into the chamber 64.

Following the deformation step required to provide communication of the two chambers, the deforming force applied to the capsule is released and the capsule will then elastically recover to the condition shown in FIG. 1 with the seal provided by the piston 54 and specifically the surfaces 42 and 62 becoming reestablished. The capsule is then inserted in a standard commercial mixing machine known as an amalgamator as shown in FIG. 3. The amalgamator 82 includes a pair of opposed fingers 84a and 84b which are vibrated or oscillated at an extremely high rate for a short period of time to thoroughly mix the mercury with the powdered materials to form an extremely dense viscous amalgam which is then ready for delivery directly from the capsule to the prepared dental cavity.

For delivery of the amalgam, the capsule is connected as shown in FIG. 4 with a modified form of syringe 66 which is characterized by a connector 68 having an annular flange 70 adapted to receive the cover end of the capsule. The connector is made of a resilient material and includes an annular bead 72 at the periphery of the flange 70 which cooperates with the shoulder 40 of the capsule flange 30 to secure the capsule to the connector. The syringe includes a flexible tubular body 74 attached to the connector 68 within which is slideably disposed a syringe rod 76 having an enlarged rod tip 78. The body 74 is connected at its end opposite the connector to a finger grip 79 through which the rod 76 extends to the actuating plunger 80. Aside from the connector 68 and the rod tip 78 which are designed to fit the capsule, the syringe is of a conventional construction.

For application of the amalgam to a prepared cavity, the capsule containing the mixed amalgam is placed in the syringe by snapping the capsule into the resilient flange of the syringe. The cap 22 is then removed and the plunger 80 of the syringe is depressed to move the rod tip 78 against the piston and sever the piston 54 from the annular neck 60. The controlled depression of the plunger advances the piston through the mixing chamber 64, engaging the amalgam and forcing the amalgam through the aperture 20 in the quantity required. The amalgam may thus be applied directly from the capsule to the prepared tooth and is neither subjected to contamination by contact with the air or other surfaces prior to deposition in the cavity. By the same token there is no opportunity for vapors to pass from the amalgam into the air except as unavoidably occurs in the patient's mouth during the placement of the amalgam. Any unused amalgam which remains in the capsule may be safely disposed of by replacing the cap 22, thus sealing the amalgam in the mixing chamber beneath the tight fitting piston 54.

Should the delivery of all of the amalgam be desired, the frusto-conical end 18 of the capsule body is sufficiently flexible to expand to the diameter of the piston, thereby allowing the piston to travel to the aperture 20 and thus eject all of the amalgam from the capsule. The capsule construction thus minimizes waste of the amalgam material which is quite expensive since the powdered metal alloy typically includes a precious metal.

The syringe may be repeatedly used with successive capsules without danger of contaminating any of the amalgam since none of the syringe elements come in contact with the amalgam and without contaminating the syringe with mercury.

The proportions of the mixing chamber have been found to have an important effect on the mixing action effected in the amalgamator as well as the ease with which the amalgam can be delivered from the chamber. In the preferred embodiment of the invention, the ratio of the length to the diameter of the mixing chamber is substantially 4:1 although an operable range of these proportions would be between 3:1 and 6:1. With a capsule having a mixing chamber diameter of 0.20 inches and a 4:1 ratio of chamber length to diameter, it has been found that 18 seconds mixing time will produce amalgam of satisfactory quality. The commonly used pestle for promoting mixing has not been found necessary with a properly proportioned mixing chamber and accordingly no provision therefore need be made.

The capsule elements are preferably molded of a plastic material and transparent polyvinylchloride (PVC) has been found to be excellent for this purpose. In a preferred embodiment, the sleeve 14, cap 22 and cover 44 are formed of a hard PVC for example of 94 Durometer hardness, while the body member 16 is formed of a relatively flexible PVC having a 80 Durometer hardness. Other materials having similar properties should also prove suitable for carrying out the invention. It is preferred that the capsule be made of a transparent material so that the condition of the contents can be readily evaluated.

Although the angle of the portion 32 of flange 30 is preferably an acute angle of 45° to the capsule body portion, modified forms of the invention could be effected using angles ranging from 15 to 85 degrees. Although any angle within this range should provide adequate passage for the mercury, an angle which provide a substantial displacement of the capsule portions is preferred since it provides a tactile as well as visual confirmation of the opened condition of the capsule chambers.

The filling of the capsule may be accomplished in several ways. In one method, the cap 22 may be secured to close the aperture 20 prior to the placement of the cover 44. In such case, the powdered material 66 and the mercury 52 are inserted from the top with the capsule in the attitude shown in FIG. 1, and the cover is then applied to separate the chambers and seal the capsule.

Alternatively, with the cover initially secured in place and the capsule inverted from its attitude shown in FIGS. 1 and 2, the mercury may first be inserted in the chamber 50 by deforming the capsule to its open position shown in FIG. 2. Upon closure of chamber 50 and the reestablishing of the seal by the piston and surfaces 42 and 62, the powder may be inserted in the mixing chamber 64 and the cap 22 applied to seal the capsule.

Manifestly, changes in details of construction can be effected by those skilled in the art without departing from the invention.

We claim:

1. A capsule for the storage of components and the mixing and delivery of dental amalgams or similar high viscosity mixtures comprising a hollow cylindrical body, an aperture in one end of said body, a demountable cap on said end of said body adapted to cover said aperture, an annular resilient flange extending outwardly from the other end of said body, a cover cooperatively engaged with said flange and including a separable piston as a portion thereof disposed to close said other end of said body, the closure of said cylindrical body by said cap at one end and said cover piston portion at the other end forming therewithin a first chamber for storage of a first amalgam constituent, the configuration of said flange and said cover forming a second chamber therebetween for storage of a second amalgam constituent, said flange being elastically deformable to permit the displacement of said body away from said cover piston portion to provide communication between said first and second chambers and combine the amalgam constituents in said first chamber for mixing therein, means for connecting said capsule to a syringe, said piston portion of said cover being detachable from said cover by actuation of a connected syringe and displaceable thereby axially along said first chamber to displace the mixed amalgam therein through said aperture upon removal of said cap.

2. The invention as claimed in claim 1 wherein said flange forms an acute angle with said capsule body thereby producing an over-center snap action thereof upon displacement of said body away from said cover.

3. The invention as claimed in claim 2 wherein the angle of said flange with respect to said capsule body is within the range of 15° to 85°.

4. The invention as claimed in claim 2 wherein said acute angle comprises substantially 45°.

5. The invention as claimed in claim 1 wherein said capsule body comprises a rigid interior sleeve and a resilient flexible body member externally adjoining said sleeve.

6. The invention as claim 5 wherein said flange extends from said resilient flexible body member.

7. The invention as claimed in claim 5 wherein the apertured end of said capsule body comprises a conical configuration formed by said flexible resilient body member.

8. The invention as claimed in claim 1 wherein said capsule body is formed of a transparent material.

9. A method of storing, mixing and delivering an amalgam for filling a prepared dental cavity comprising the steps of:

providing a capsule having first and second chambers separated by a piston, said capsule including an annular outwardly extending resilient flange forming a part of said second chamber, said flange being elastically deformable to bring said chambers into communication, the first of said chambers having an elongated configuration and being closed at one end by said piston and at the other end by a detachable cap;

introducing predetermined quantities of the amalgam constituents into said separated chambers for storage therein until the amalgam is needed;

upon need for the amalgam, deforming said capsule flange to permit the constituent of said second chamber to flow past said piston into said first chamber to join the constituent therein;

placing said capsule in an amalgamator to mix the amalgam constituents;

applying a syringe to said capsule for actuation of said piston;

removing said cap to permit delivery of the amalgam from the capped end of the capsule; and selectively advancing said piston into said first chamber to transfer the mixed amalgam directly into the prepared dental cavity.

* * * * *